US010518264B2

(12) United States Patent
Conoci et al.

(10) Patent No.: US 10,518,264 B2
(45) Date of Patent: Dec. 31, 2019

(54) MICROREACTOR AND METHOD FOR LOADING A LIQUID

(71) Applicant: STMicroelectronics S.r.l., Agrate Brianza (IT)

(72) Inventors: Sabrina Conoci, Tremestieri Etneo (IT); Maria Eloisa Castagna, Catania (IT); Massimo Orazio Spata, Catania (IT)

(73) Assignee: DISTRETTO TECNOLOGICO SICILIA MICRO E NANO SISTEMI S.C.A.R.L., Catania (IT)

(*) Notice: Subject to any disclaimer, the term of this patent is extended or adjusted under 35 U.S.C. 154(b) by 1007 days.

(21) Appl. No.: 14/221,033

(22) Filed: Mar. 20, 2014

(65) Prior Publication Data

US 2014/0291152 A1 Oct. 2, 2014

(30) Foreign Application Priority Data

Mar. 29, 2013 (IT) .............................. TO2013A0264

(51) Int. Cl.
*B01L 3/00* (2006.01)
*C12Q 1/6844* (2018.01)

(52) U.S. Cl.
CPC ......... *B01L 3/50273* (2013.01); *B01L 3/5085* (2013.01); *B01L 3/502784* (2013.01); *C12Q 1/6844* (2013.01); *B01L 3/50851* (2013.01); *B01L 3/502723* (2013.01); *B01L 2200/0642* (2013.01); *B01L 2300/0864* (2013.01); *B01L 2300/166* (2013.01); *B01L 2400/0406* (2013.01); *B01L 2400/0427* (2013.01)

(58) Field of Classification Search
CPC ....... B01L 2300/161; B01L 2300/0645; B01L 2300/0829
USPC .................................................. 422/552, 553
See application file for complete search history.

(56) References Cited

U.S. PATENT DOCUMENTS

| | | | | |
|---|---|---|---|---|
| 6,306,348 | B1 | 10/2001 | Havens | |
| 6,444,106 | B1 * | 9/2002 | Mcbride | B01L 3/50273 204/450 |
| 8,163,150 | B2 | 4/2012 | Vann | |
| 2005/0056540 | A1 * | 3/2005 | Ramstad | G01N 27/44743 204/451 |

(Continued)

FOREIGN PATENT DOCUMENTS

| | | |
|---|---|---|
| EP | 1364710 | 11/2003 |
| FR | 2884242 | 7/2011 |
| IT | IO 38301 | 11/2013 |

OTHER PUBLICATIONS

Oprins et al., "On-Chip Electrowetting Cooling", Webpage from Liquid Cooling, May 1, 2006.

*Primary Examiner* — Natalia Levkovich
(74) *Attorney, Agent, or Firm* — Seed IP Law Group LLP

(57) ABSTRACT

A microreactor includes: a substrate (2; 102; 202) made of semiconductor material; a plurality of wells (5; 105; 205) separated by walls (6; 106; 206) in the substrate (2; 102; 202); a dielectric structure (7; 107; 207*a*, 207*b*) coating at least the top of the walls (6; 106; 206); a cap (3; 103; 203), bonded to the substrate (2; 102; 202) and defining a chamber (10; 110; 210) above the wells (5; 105; 205); and a biasing structure (2, 8, 13; 102, 108, 113; 202, 208*a*, 208*b*, 213), configured for setting up a voltage (VB) between the substrate (2; 102; 202) and the chamber (10; 110; 210).

13 Claims, 4 Drawing Sheets

(56) References Cited

U.S. PATENT DOCUMENTS

| | | | |
|---|---|---|---|
| 2006/0078984 | A1 | 4/2006 | Moyle |
| 2012/0106238 | A1 | 5/2012 | Gareth |

* cited by examiner

MICROREACTOR AND METHOD FOR LOADING A LIQUID

PRIOR RELATED APPLICATIONS

This application claims priority to Italian Patent Application No. TO2013A000264 of Mar. 29, 2013 and incorporated by reference in its entirety herein.

FEDERALLY SPONSORED RESEARCH STATEMENT

Not applicable.

REFERENCE TO MICROFICHE APPENDIX

Not applicable.

FIELD OF THE DISCLOSURE

The present disclosure relates to a microreactor and to a method for loading a liquid into the microreactor.

BACKGROUND OF THE DISCLOSURE

As is known, some types of microreactors, such as microreactors for biochemical analyses, comprise arrays of wells for receiving small volumes of reagents in the form of liquids or gels, especially water-based ones, and/or given volumes of specimens to be analyzed. Microreactors of this type respond, amongst other things, to the widespread need of increasing the level of parallelism in the execution of analysis procedures, for example for diagnostic or experimental purposes. Each well may be prepared with different reagents, and hence various analytical procedures may be conducted simultaneously on a single biological sample.

In a typical application, the wells are prepared for performing reactions of amplification of nucleic acids, for example by PCR (Polymerase Chain Reaction). In addition to the mixture of reagents necessary for amplification, loaded in each well are respective detector sequences, which comprise single stranded oligonucleotides capable of binding to corresponding DNA or RNA sequences that may be present in the biological sample. This way, each well may be dedicated to recognition of a specific target sequence (for example, corresponding to a specific pathogenic agent).

Handling of small volumes of biological sample may, however, create difficulties, particularly in loading of the wells. All the wells must receive a sufficient amount of biological sample. Once loading has been carried out, moreover, the contents of each well must be kept segregated from those of the other wells during the reactions in order to prevent any contamination that might jeopardize the outcome of the processes.

The biological sample may be introduced into the wells manually, using pipettes. In this case, the microreactors are initially uncovered to enable access to the wells, and are closed only subsequently. Manual loading presents evident limits both owing to the impossibility of treating very small volumes (a few microliters) and because contaminations are relatively likely to occur.

In other microreactors, the specimen is loaded in a common reservoir and distributed to the wells via microchannels, in which the fluid advances by capillary action. In this case, very small volumes of fluid can be treated. But, problems may arise owing to the formation of bubbles in the microchannels, thus impeding flow and reducing the amount of available liquid.

When capillary forces are involved, air bubbles may easily remain trapped during loading. The geometry and the affinity of the specimen with the material forming the microchannels may produce highly unstable menisci. The edges of the menisci may join up in given conditions, and the air bubbles may be trapped inside the liquid. A single air bubble may occupy a relatively wide portion of the microchannels and prevent an adequate volume of specimen from reaching one or more wells. Analysis may be impaired because important process parameters, such as volume, equilibrium of the reagents, pressure and temperature, are affected by the presence of bubbles.

The aim of the present disclosure is to provide a microreactor and a method for loading a liquid into a microreactor that will enable the limitations described to be overcome.

SUMMARY OF THE DISCLOSURE

According to the present disclosure, a microreactor and a method for loading a liquid into the microreactor are provided.

The microreactor includes a substrate made of semiconductor material; a plurality of wells separated by walls in the substrate; a dielectric structure coating at least the top of the walls; a cap, bonded to the substrate and defining a chamber above the wells; and a biasing structure, configured for setting up a voltage between the substrate and the chamber. This structure allows fluid in the chamber above the wells to enter the wells when voltage is applied through the electrowetting phenomena. Bubbles are avoided and all wells can be simultaneously filled.

DESCRIPTION OF DRAWINGS

For a better understanding of the disclosure, some embodiments thereof will now be described, purely by way of non-limiting example and with reference to the attached drawings, wherein.

DETAILED DESCRIPTION

Figure 1:
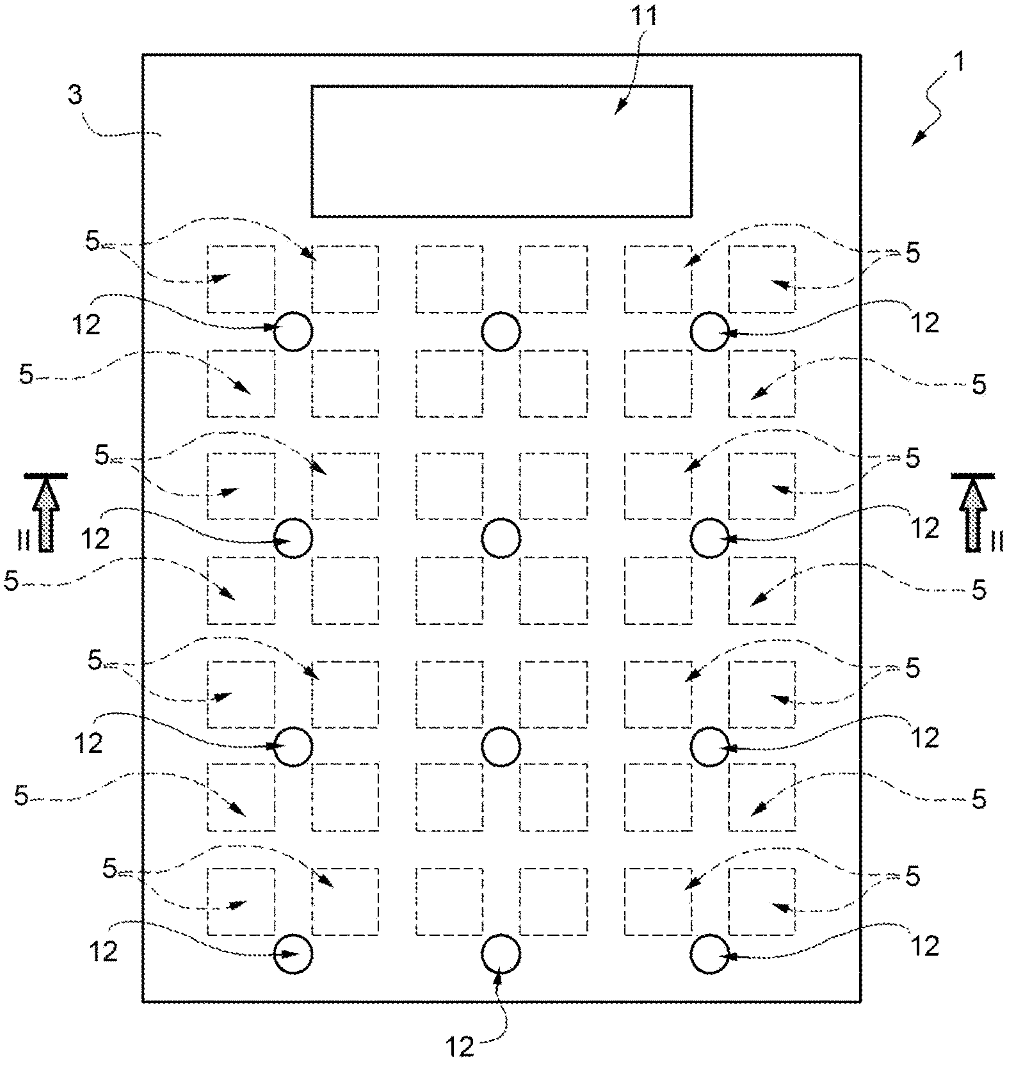
FIG. 1 is a simplified top plan view of a microreactor according to one embodiment of the present disclosure.
Figure 2:
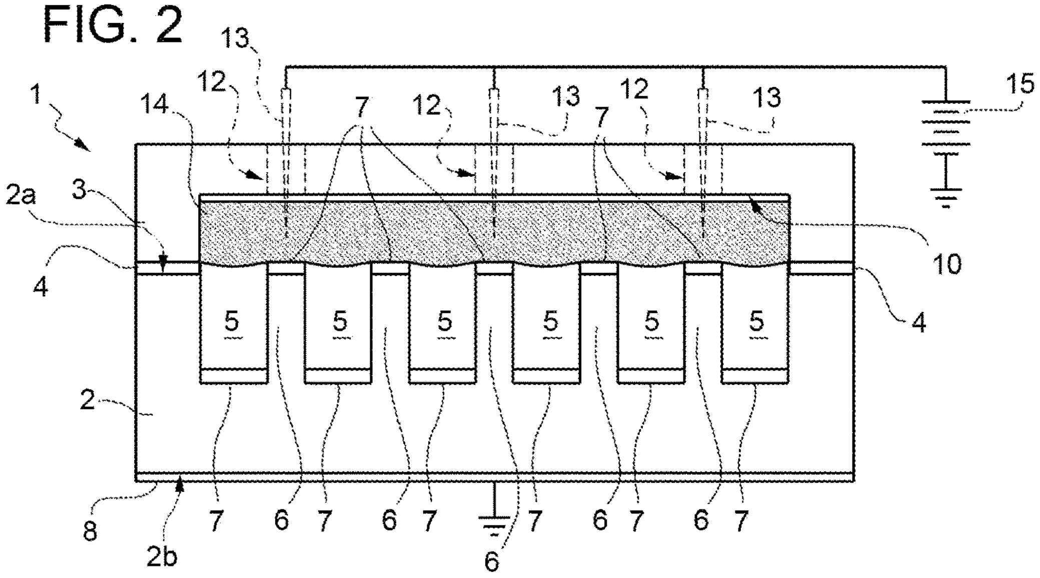
FIG. 2 is a cross section of the microreactor of FIG. 1, taken along the line II-II of FIG. 1.

In FIGS. 1 and 2, a microreactor according to one embodiment of the present disclosure is designated as a whole by the reference number 1. The microreactor 1 may be, for example, of the type used for biochemical analyses, particularly for reactions of amplification of nucleic acids and identification of specific target sequences. It is understood, however, that the disclosure is not limited to this type of application and may advantageously be exploited for providing microreactors of any kind.

The microreactor 1 comprises a semiconductor substrate 2, for example doped monocrystalline silicon, and a cap 3 bonded to a top face 2*a* of the substrate 2 through a bonding layer 4. By "top face" is meant, here and in what follows, a face of the substrate 2 that, in use, is to face upwards, such that the cap 3 prevents exit of the fluid that has been loaded into the microreactor 1.

The substrate 2 contains a plurality of wells 5, arranged in arrays and separated from one another by walls 6. The top of the walls 6 (i.e., in practice the top face 2*a* of the substrate 2) and the bottom of the wells 5 are coated by dielectric regions 7, whereas vertical faces of the walls 6 are exposed (e.g., uncoated).

The wells 5 may have, for example, a rectangular or circular shape. In one embodiment, the wells 5 have dimensions such that the surface tension of the fluid to be loaded into the microreactor 1, particularly the surface tension of the water for samples of biological fluids, is sufficient to prevent spontaneous filling of the wells 5 themselves. For example, the wells 5 have a square cross section with a side of approximately 800 μm and have a depth of approximately 400 μm.

The substrate 2 is moreover provided with a first biasing electrode 8, which, in one embodiment, is provided on a bottom face 2*b*.

The cap 3 is bonded to the top face 2*a* of the substrate 2 and is arranged for covering the wells 5. Inside, the cap 3 has a cavity that defines a chamber 10 together with the substrate 2. In greater detail, the chamber 10 extends over the entire array of the wells 5 and is accessible from outside through an inlet opening 11 for loading a fluid to be processed, for example a biological sample. The chamber 10 is shaped in such a way that the fluid introduced through the inlet opening 11 distributes over the top of all the wells 5. In some embodiments, the volume of the chamber 10 is smaller than or substantially equal to the sum of the volumes of all the wells 5 (for example, 20 μl).

The cap 3 moreover has biasing openings 12 configured to enable introduction of one or more needle-shaped second electrodes 13 within the chamber 10, while preventing exit of the fluid. For this purpose, the biasing openings 12 have a cross section of a size such as to prevent spontaneous rising of the fluid by capillary action. For example, the cross section of the biasing openings 12 has dimensions smaller than the dimensions of the wells 5. The openings 12 enable the exit of any air present in the chamber 10 during introduction of liquid into the chamber 10 itself.

In one embodiment, the biasing openings 12 are arranged in positions corresponding to walls 6 or crossings between walls 6 that delimit adjacent wells.

The microreactor 1 exploits the electrowetting phenomenon.

When a volume of liquid 14, such as a biological sample in the example described, is loaded into the microreactor 1 through the inlet opening 11, the chamber 10 is filled. However, the liquid 14 does not manage to penetrate into the wells 5 as a result of the surface tension and of the dimensions of the wells 5 themselves.

Through the biasing openings 12, one or more second electrodes 13 are hence brought into contact with the liquid 14 inside the chamber 10. Using an electric power-supply source 15, the first biasing electrode 8 and the second biasing electrodes 13, a biasing voltage VB is applied between the substrate 2 and the liquid 14. In practice, the entire substrate 2 functions as a biasing electrode.

The liquid 14 and the substrate 2 are initially insulated both by the dielectric regions 7 that are located at the top of the walls 6, and by the air contained in the wells 5. In general, in a condition where a liquid and an electrode are separated by an insulating region and are subjected to a voltage, the forces that act within the liquid cause wettability to increase. In the example described, in practice, the biasing voltage VB causes the surface tension of the liquid 14 to be overcome, and brings about an interruption in continuity. It should be noted that the arrangement of the second electrodes 13 above walls 6 or crossings between walls 6 favors division of the volume of liquid 14.

Figure 3:
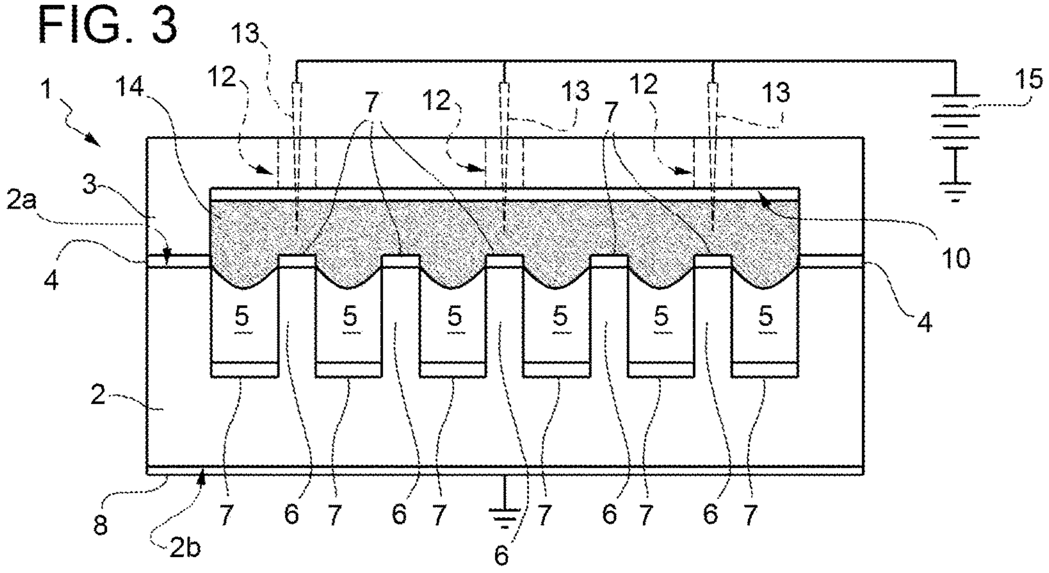
FIGS. 3 and 4 show the view of FIG. 2 in successive steps during loading of a liquid.

The liquid 14 thus begins to penetrate into the wells 5, filling of which is started, as shown in FIG. 3. When the liquid 14 comes into contact with the exposed faces of the walls 6, its conditions are modified because the electrical insulation from the substrate 2 ceases locally. However, the portion of liquid 14 inside the wells 5 is subjected to capillary forces that start to prevail, thus filling the wells.

Figure 4:
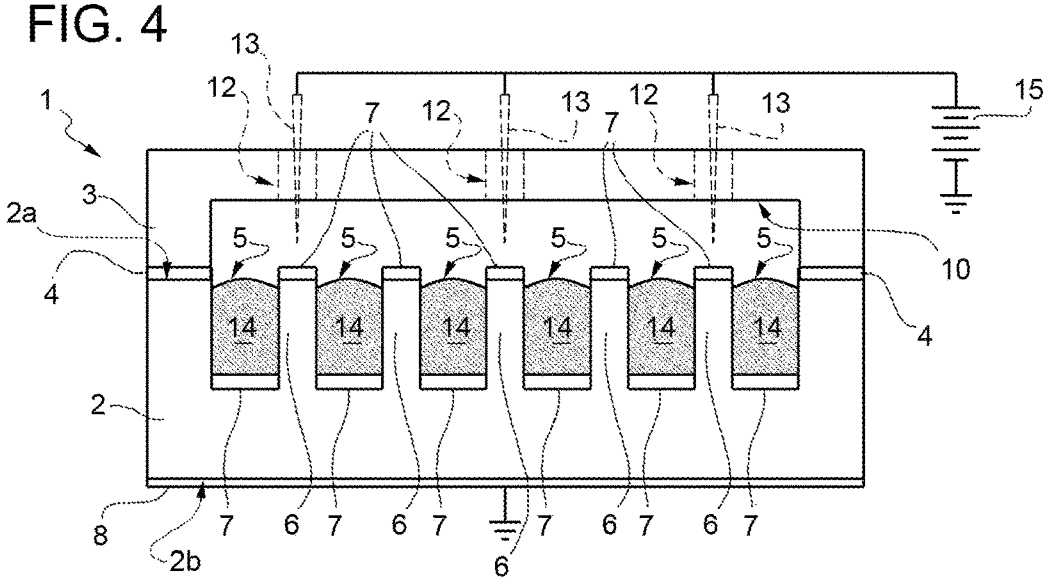

Once the surface tension of the liquid 14 has been overcome, the wells 5 are filled as a result of the capillary forces. In this way, the initial volume of liquid is divided into a plurality of drops that occupy respective wells 5 and are separated from one another, as shown in FIG. 4.

The capillary forces are exploited only in order to complete the filling of the wells, and there is no risk of formation of bubbles in the liquid.

Once the liquid 14 has been distributed in the wells 5, the electrical-supply source 15 is turned off or disconnected from the microreactor 1 in order to remove the biasing voltage VB and prevent waste of energy.

In addition, the chamber 10 may be filled with oil once the wells are loaded to prevent evaporation of the liquid 14 during the reactions, which may comprise thermal cycles, as in the example of nucleic-acid amplification by PCR. The openings 11, 12 may be sealed, for example with wax, before performing the reactions envisaged for the microreactor 1, but this may not be needed with an oil cap.

The microreactor described advantageously enables handling of extremely small volumes of liquid (a few microliters or even fractions of microliters) and introduction of the liquid into the wells from the chamber without any need for mechanical parts and preventing the formation of bubbles.

Figure 5:
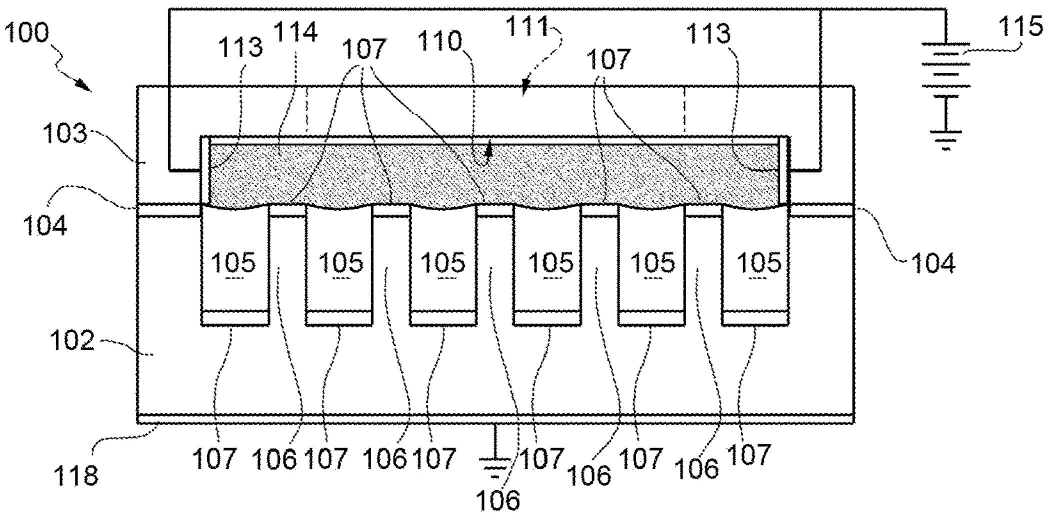
FIG. 5 is a cross section of a microreactor according to a different embodiment of the disclosure.

According to the embodiment illustrated in FIG. 5, a microreactor 100 comprises a substrate 102 made of semiconductor material, in which wells 105 are provided, and a cap 103, bonded to the substrate 102 through a bonding layer 104 and having a cavity that defines a chamber 110 above the plurality of wells 105.

Dielectric regions 107 coat the bottom of the wells 105 and the top of walls 106 that separate the wells from one another, while lateral surfaces of the walls 106 are exposed. The substrate 102 is provided with a first biasing electrode 118 on a face opposite to the wells 105.

The cap 103 has an inlet opening 111 for introduction of a liquid 114 and venting openings (not shown) to enable exit of air from the chamber 110. The cap 103 is moreover provided with a second biasing electrode 113 that extends along side walls of the cavity defining the chamber 110, as far as a margin adjacent to the substrate 102. In this way, the second biasing electrode 113 is in contact with a liquid introduced into the chamber 110 also when the liquid penetrates into the wells 105 and the level starts to decrease. The substrate 102 defines a second electrode that enables the liquid to penetrate into the wells 105 by electrowetting.

Figure 6:
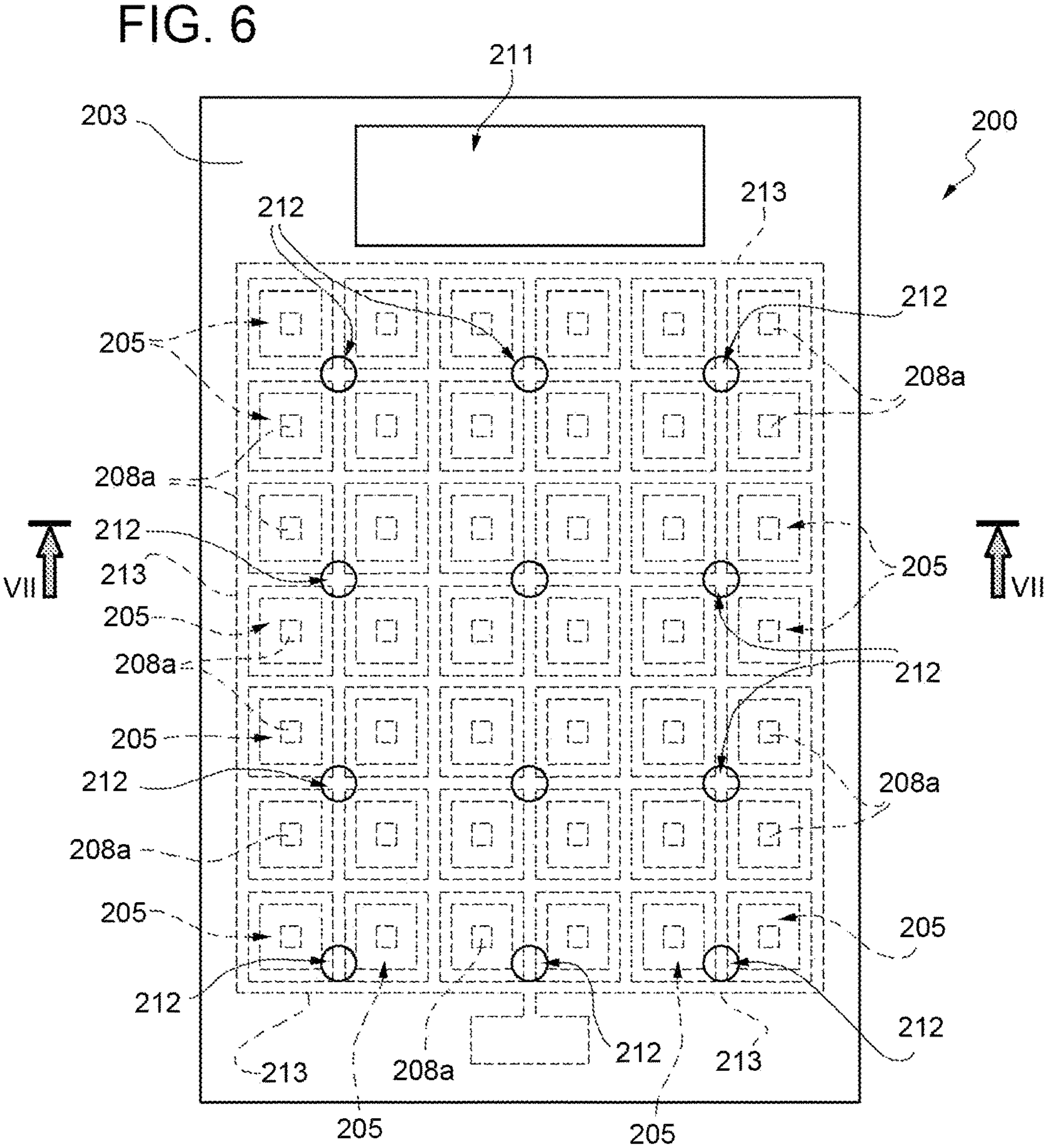
FIG. 6 is a simplified top plan view of a microreactor according to a further embodiment of the present disclosure.
Figure 7:
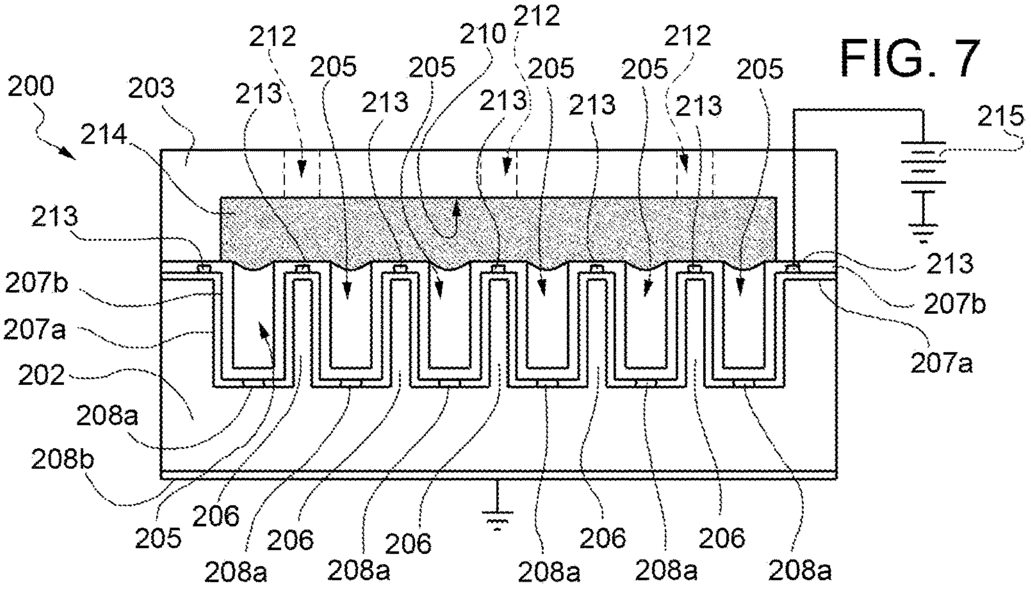
FIG. 7 is a cross section of the microreactor of FIG. 6, taken along the line VII-VII of FIG. 6.

FIGS. 6 and 7 illustrate a further embodiment of the disclosure. In this case, a microreactor 200 comprises a substrate 202 made of semiconductor material and a cap 203 bonded to the substrate 202 through a bonding layer (not shown).

Provided in the substrate 202 are wells 205 arranged in arrays and separated by walls 206. A first dielectric layer 207*a* and a second dielectric layer 207*b*, made for example of silicon oxide, coat the lateral surface and the top of the walls 206, as likewise the bottom of the wells 205.

First biasing electrodes 208*a*, 208*b* are located, respectively, on the bottom of the wells 205 and on a face of the substrate 202 opposite to the wells 205. The first biasing electrodes 208*a* are housed in openings of the first dielectric layer 207*a* and are hence in electrical contact with the substrate 202. The second dielectric layer 207*b* coats the first biasing electrodes 208*a*.

A second biasing electrode 213, in the form of a grid of conductive material, for example copper or aluminium, is incorporated between the first dielectric layer 207*a* and the second dielectric layer 207*b* and extends on the top of the walls 206 that divide the wells 205 from one another. Portions of the second biasing electrode 213 hence surround each well 205.

The first biasing electrodes 208*a*, 208*b* and the second biasing electrode 213 are thus electrically insulated from one another.

The cap 203 has a cavity that defines a chamber 210 above the wells 205. The cap 203 moreover has an inlet opening 211 for enabling introduction of a liquid 214 into the chamber 210 and venting openings 212 for enabling exit of the air from the chamber 210.

An electrical-supply source 215 enables applying a biasing voltage VB between the first electrodes 208*a*, 208*b* and the second electrode 213.

The electrical field that is set up in the liquid 214 as a result of the biasing voltage VB between the first electrodes 208*a*, 208*b* and the second electrode 213 modifies the angle of contact with the surface of the second dielectric layer 207*b*, with which the liquid 214 is in contact, modifying the wettability. Once the liquid 214 has overcome the surface tension, it penetrates into the wells 205 and distributes therein dividing up.

Figure 8:
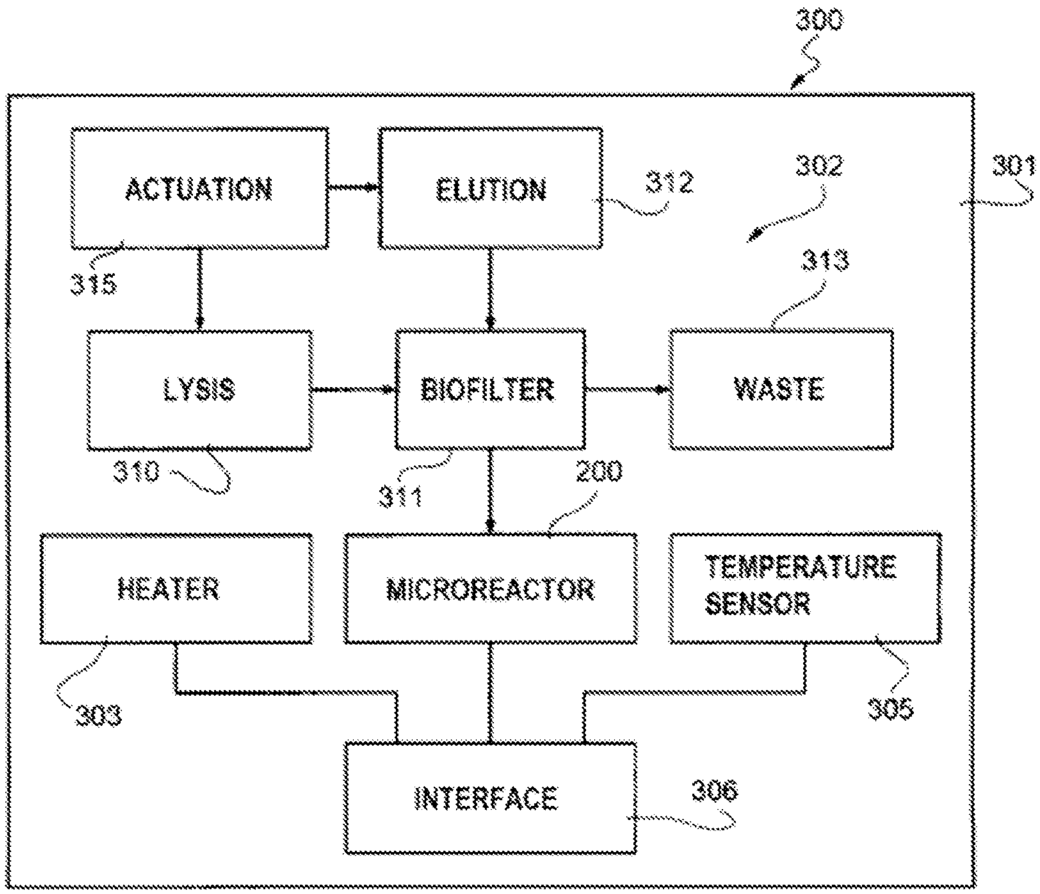
FIG. 8 is a simplified block diagram of a cartridge for biochemical analyses incorporating a microreactor according to one embodiment of the present disclosure.

With reference to FIG. 8, a cartridge 300 for biochemical analyses, in particular analyses of nucleic acids, comprises a support 301, for example a printed-circuit board, which houses a sample-preparation structure 302 and a microreactor according to one embodiment of the disclosure. In the example of FIG. 8, in particular, the support 301 houses the microreactor 200 described previously with reference to FIGS. 6 and 7. Moreover, the cartridge 300 comprises a heater 303 and a temperature sensor 305, arranged on the support 301 and thermally coupled to the microreactor 200. An interface 306 enables electrical connection of the biasing electrodes 208*a*, 208*b*, 213, of the heater 303, and of the temperature sensor 305 with an external analysis apparatus. In one embodiment, the support 301 is a semiconductor chip and defines the substrate in which the wells of the microreactor 200 are provided.

The sample-preparation structure comprises a lysis chamber 310, a biofilter 311, an elution chamber 312, a waste chamber 313 and a microfluidic actuation circuit 315, for example including a micropump and microfluidic valves and not described in detail herein.

The lysis chamber 310 contains reagents that enable a preliminary preparation of the biological sample to be carried out. In particular, in the lysis chamber the nucleated cells present in the biological sample to be analyzed are broken up, and the DNA strands of the nuclei are extracted. The lysis chamber 310 is fluidly coupled to the biofilter 311 and to the waste chamber 313. Once the sample has been prepared, the microfluidic actuation circuit 315 displaces the sample itself to the waste chamber 313 through the biofilter 311. The biofilter 311 comprises a chamber having a surface made of silicon oxide, to which the DNA strands extracted from the cells remain anchored as they travel towards the waste chamber 313. The remaining material, instead, is not withheld and is collected in the waste chamber 313.

The elution chamber 312 contains known solutions for flushing the biofilter 311, which enable release of the anchorage of the DNA strands to the silicon-oxide surface. The solution is displaced by the microfluidic actuation circuit 315 from the elution chamber 312 towards the microreactor 301 through the biofilter 311. The DNA strands are thus released and transferred in solution to the microreactor 200, the wells 205 of which (here not shown) contain respective combinations of reagents for recognition of specific nucleotide sequences. In particular, the wells 205 may contain respective specific target nucleotide sequences or DNA probes capable of binding to complementary sequences that may be present in the sample.

Figure 9:
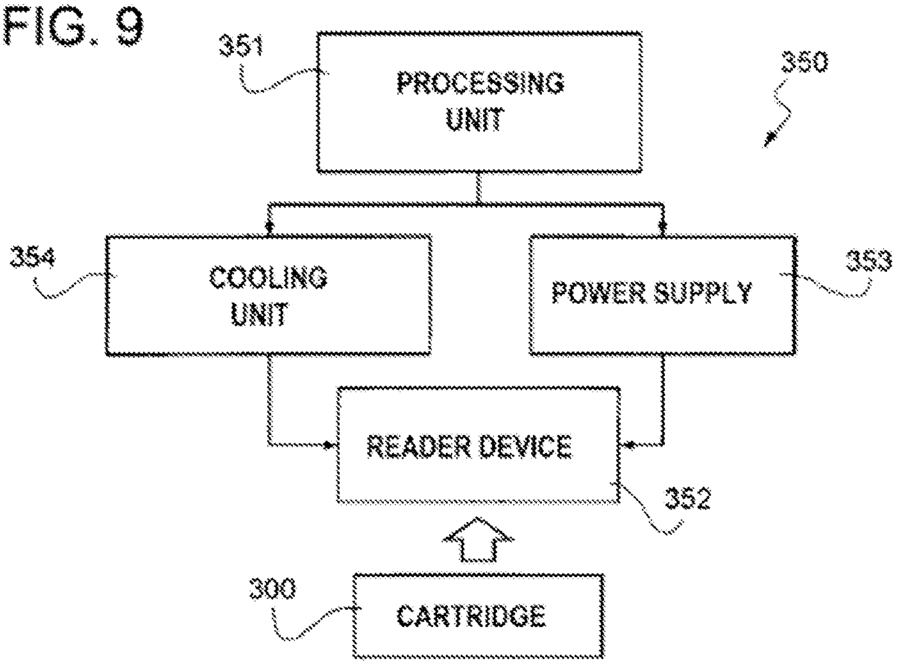
FIG. 9 is a simplified block diagram of an apparatus for analysis that uses the cartridge of FIG. 8.

For carrying out a process of analysis, the cartridge 300 is inserted into an analysis apparatus 350, illustrated in FIG. 9. The analysis apparatus 350 comprises a processing unit 351, a reader device 352, configured to receive the cartridge 300, a power supply 353, and a cooling unit 354, both of which are controlled by the processing unit 352. The cooling unit 354 may comprise, for example, a Peltier module or a fan and is thermally coupled to the microreactor 200 (not shown in FIG. 9) of the cartridge 300 loaded in the reader device 352.

The processing unit 351 is configured to control the electrodes 208*a*, 208*b*, 213 (not shown) for causing a sample to penetrate into the wells 205 from the chamber 210 (which are not shown).

The heater 303 and the temperature sensor 305 (neither of which is shown) of the cartridge 300 are respectively coupled to the power supply 353 and to the processing unit 351 through the interface 306 (not shown). The processing unit 351 controls the heater 303 and the cooling unit 354 on the basis of the temperature detected by the temperature sensor 305 for subjecting the microreactor 200 and the solutions contained therein to a plurality of thermal cycles according to a programmed temperature profile. The thermal cycles, in one embodiment, enable reactions of DNA amplification to be performed, in particular according to a PCR protocol.

The reader device 352, for example of an optical type, is configured for detecting the presence of target nucleotide sequences on the basis of the properties of the reaction results present in the wells of the microreactor 200.

Finally, it is evident that modifications and variations may be made to the microreactor and to the method described, without thereby departing from the scope of the present disclosure, as defined in the annexed claims. In particular, we have shown a single chamber over a plurality of wells, and such a device is appropriate for doing several different analyses of a single sample. However, a plurality of chambers, each covering a plurality of wells can easily be provided and thus allowing for the simultaneous analyses of more than one sample in the same cartridge.

The invention claimed is:

1. A microreactor comprising:

a substrate of a semiconductor material;

a plurality of wells separated by walls in the substrate;
a dielectric structure covering at least tops of the walls;
a cap bonded to the substrate and defining a chamber above the wells, the chamber being directly open to each of the wells; and,
a biasing structure that, in use, establishes a first voltage on the substrate and a second voltage in the chamber, wherein:
the biasing structure comprises a first electrode electrically connected to the substrate and directly underlying each of the wells, the biasing structure, in use, establishing the first voltage under each of the wells; and
the biasing structure comprises needle-shaped second electrodes and the cap has biasing openings for introduction of the second electrodes into the chamber, the second electrodes, in use, establishing the second voltage in the chamber above each of the wells.

2. The microreactor according to claim 1, wherein:
the cap has an inlet opening for introduction of the liquid into the chamber.

3. The microreactor according to claim 1, wherein the wells have such dimensions as to prevent spontaneous entrance of the liquid when the liquid is aqueous.

4. The microreactor according to claim 1, wherein the biasing structure comprises the substrate.

5. The microreactor according to claim 1, wherein the substrate has a top surface and a bottom surface, the wells extending into the substrate from the top surface and the first electrode contacting the bottom surface of the substrate.

6. The microreactor according to claim 1, wherein the biasing openings are arranged in positions corresponding to the walls.

7. The microreactor according to claim 6, wherein lateral surfaces of the walls are exposed.

8. The microreactor according to claim 1, wherein the biasing structure comprises an electrical supply source.

9. A microfluidic cartridge comprising:
a support; and
a microreactor on the support, the microreactor including:
a substrate of a semiconductor material;
a plurality of wells separated by walls in the substrate;
a dielectric structure covering at least tops of the walls;
a cap bonded to the substrate and defining a chamber above the wells, the chamber being directly open to each of the wells; and,
a biasing structure that, in use, establishes a first voltage on the substrate and a second voltage in the chamber, wherein:
the biasing structure comprises a first electrode electrically connected to the substrate and directly underlying each of the wells, the biasing structure, in use, establishing the first voltage under each of the wells; and
the biasing structure comprises needle-shaped second electrodes and the cap has biasing openings for introduction of the second electrodes into the chamber, the second electrodes, in use, establishing the second voltage in the chamber above each of the wells.

10. The cartridge according to claim 9, comprising:
a microfluidic circuit fluidly coupled to the microreactor;
a heater and a temperature sensor, arranged on the support and thermally coupled to the microreactor; and
an interface configured to electrically couple the heater and temperature sensor to an analysis equipment.

11. Analysis equipment comprising:
a reader device;
a cartridge positioned in the reader device, the cartridge including:
a support; and
a microreactor according to on the support, the microreactor including:
a substrate of a semiconductor material;
a plurality of wells separated by walls in the substrate;
a dielectric structure covering at least tops of the walls;
a cap bonded to the substrate and defining a chamber above the wells, the chamber being directly open to each of the wells; and
a biasing structure that, in use, establishes a first voltage on the substrate and a second voltage in the chamber, wherein:
the biasing structure comprises a first electrode connected to the substrate and directly underlying each of the wells, the biasing structure, in use, establishing the first voltage under each of the wells; and
the biasing structure comprises needle-shaped second electrodes and the cap has biasing openings for introduction of the second electrodes into the chamber, the second electrodes, in use, establishing the second voltage in the chamber above each of the wells.

12. The cartridge according to claim 9, wherein the substrate has a top surface and a bottom surface, the wells extending into the substrate from the top surface and the first electrode contacting the bottom surface of the substrate.

13. The analysis equipment according to claim 11, wherein the substrate has a top surface and a bottom surface, the wells extending into the substrate from the top surface and the first electrode contacting the bottom surface of the substrate.

* * * * *